United States Patent
Lang et al.

(10) Patent No.: US 9,414,759 B2
(45) Date of Patent: Aug. 16, 2016

(54) SURFACE ELECTRODE DESIGN THAT CAN BE LEFT IN PLACE DURING MR IMAGING

(75) Inventors: Michael Lang, Winnipeg (CA); Labros Petropolous, Winnipeg (CA); Mark Alexiuk, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 791 days.

(21) Appl. No.: 13/311,677

(22) Filed: Dec. 6, 2011

(65) Prior Publication Data
US 2013/0141093 A1 Jun. 6, 2013

(51) Int. Cl.
| A61B 5/0424 | (2006.01) |
| A61B 5/055 | (2006.01) |
| A61B 5/0408 | (2006.01) |
| G01R 33/28 | (2006.01) |
| G01R 33/567 | (2006.01) |

(52) U.S. Cl.
CPC .......... *A61B 5/04087* (2013.01); *G01R 33/288* (2013.01); *G01R 33/5673* (2013.01); *A61B 5/0424* (2013.01); *A61B 5/055* (2013.01); *A61B 2562/0223* (2013.01)

(58) Field of Classification Search
USPC .......... 324/300–322; 600/407–435, 393, 509, 600/554; 382/128–131; 606/79, 80
See application file for complete search history.

(56) References Cited

U.S. PATENT DOCUMENTS

| 5,552,315 A | 9/1996 | Slininger et al. |
| 5,782,241 A | 7/1998 | Felblinger |
| 6,032,063 A | 2/2000 | Hoar |
| 6,812,703 B2 * | 11/2004 | de Swiet et al. ............. 324/318 |
| 7,993,167 B2 | 8/2011 | Keightley |
| 8,052,688 B2 * | 11/2011 | Wolf, II ......................... 606/80 |
| 8,175,679 B2 * | 5/2012 | Gerhart et al. ................ 600/423 |
| 8,473,029 B2 * | 6/2013 | Gerhart et al. ................ 600/411 |
| 8,494,620 B2 * | 7/2013 | Rey ................................ 600/509 |
| 8,500,738 B2 * | 8/2013 | Wolf, II ......................... 606/79 |
| 2003/0078646 A1 | 4/2003 | Axelgaard |
| 2003/0220578 A1 | 11/2003 | Ho et al. |
| 2004/0113617 A1 * | 6/2004 | de Swiet et al. ............. 324/318 |
| 2006/0279284 A1 * | 12/2006 | Vaughan ...................... 324/318 |
| 2008/0086140 A1 * | 4/2008 | Wolf .............................. 606/79 |
| 2008/0204021 A1 * | 8/2008 | Leussler et al. .............. 324/318 |
| 2009/0171187 A1 * | 7/2009 | Gerhart et al. ................ 600/421 |
| 2009/0306494 A1 | 12/2009 | Scarth et al. |
| 2010/0244826 A1 | 9/2010 | Schmidig |
| 2011/0082359 A1 * | 4/2011 | Rey ................................ 600/393 |
| 2011/0159371 A1 | 6/2011 | Lyden et al. |
| 2011/0160826 A1 | 6/2011 | Schmalhurst et al. |
| 2012/0022394 A1 * | 1/2012 | Wolf, II ......................... 600/554 |
| 2012/0226143 A1 * | 9/2012 | Gerhart et al. ................ 600/423 |
| 2013/0141093 A1 * | 6/2013 | Lang et al. ................... 324/309 |
| 2013/0317340 A1 * | 11/2013 | Wolf, II ......................... 600/409 |

* cited by examiner

*Primary Examiner* — Melissa Koval
*Assistant Examiner* — Tiffany Fetzner
(74) *Attorney, Agent, or Firm* — Adrian D. Battison; Ade & Company Inc.

(57) ABSTRACT

For use in MR imaging of a patient a plurality of surface electrodes such as ECG or defibrillator are provided for obtaining electrical signals for determining electrical activity within the body of the patient and remain in place during the MR imaging. The surface electrodes include a quick disconnect wire for carrying the signals to a signal processing system to be removed during the MR imaging to prevent heating. Each electrode comprises a conductive layer divided by slits into separate side by side sections to reduce eddy currents which are induced in the surface electrodes when they are exposed to variations in the magnetic field. The sections all are connected through the layer to the conductive location to allow the signal therefrom to be connected to the communication conductor.

20 Claims, 6 Drawing Sheets

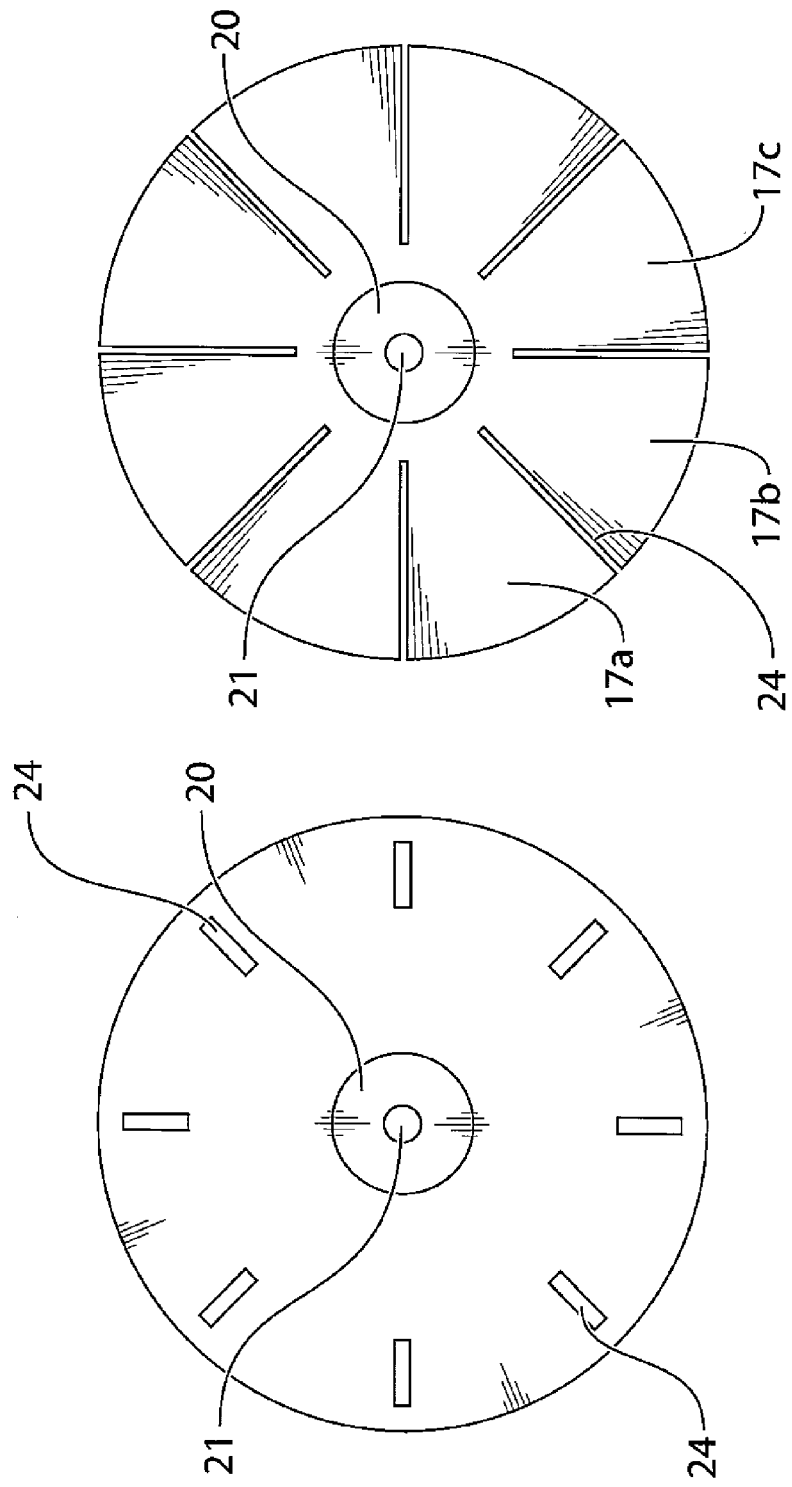

SURFACE ELECTRODE DESIGN THAT CAN BE LEFT IN PLACE DURING MR IMAGING

This invention relates to a surface electrode design that can be left in place during MR imaging.

BACKGROUND OF THE INVENTION

Surface electrodes are wired electrical connections commonly used to measure biological signals. These electrodes support patient monitoring by measuring electrical signals related to brain function (EEG) and heart activity (ECG) etc. Typically, many electrodes are distributed on the surface of the head or body to collect, in aggregate, diagnostic information. For example, 12-lead ECG can identify characteristic information about an ST-segment elevated myocardial infarction, a common type of heart attack.

Surface electrodes are also used to track invasive devices such as the St Jude Medical ENSITE NAVX (trademark) catheter tracking system. This device uses three pairs of surface electrodes positioned to be create roughly perpendicular electric fields through the body. A similar array of electrodes is used by Biosense Webster CARTO3 system. These tracking systems are also known as electro-anatomical mapping systems due to their use in electrophysiology.

Catheter tracking is particularly valuable in electrophysiology procedures to treat atrial fibrillation as the ablations must create a permanent conduction block which depends on transmurality (completely through the tissue) and contiguity of the scar.

However, surface electrodes are not designed for use in an MR. The patch component is a conductive surface and therefore susceptible to eddy currents from the scanner magnetic gradients and RF pulses. These currents degrade image quality. The wire acts as an antenna with respect to the RF pulses and the induced current can be a burn risk for the patient.

These issues, MR image degradation and safety risk, generally require that the surface electrodes must be removed from the patient before MR imaging occurs. However, this is not the optimal workflow as the MR post-interventional imaging may reveal a need for further immediate treatment. In this case of immediate retreatment, the electrodes need to be re-placed and the intervention setup re-done. This extra effort also occurs for the above system but may require that the impedance map of the heart be re-acquired. This is done by tracing the catheter along the endocardial surface and post-processing to isolate regions of interest.

The majority of cardiac interventions using ECG leads and surface electrodes, however, still occur in conventional labs where MR is not used.

Interventions guided only by cardiac MR or multi-modality interventions are driving modifications to the existing surface electrodes.

U.S. Pat. No. 5,782,241 (Felblinger) issued Jul. 21, 1998, U.S. Pat. No. 6,032,063 (Hoar) issued Feb. 29 2000 and US published application 201010233826 (Schmidig) published Sep. 30 2010 all relate to electrode arrangements designed so that they can remain in place in an MR magnet. U.S. Pat. No. 7,993,167 (Keightley) issued Aug. 9 2011 discloses a shielded electrode.

SUMMARY OF THE INVENTION

It is one object of the invention to provide an improved electrode for use in MR imaging.

According to one aspect of the invention there is provided a method for MR imaging of a patient comprising providing an MR magnet to generate a magnetic field to be applied to the patient;

generating an RF pulse in the magnetic field to be applied to the patient such that the imaged part of the patient generates an MR signal in response to the magnetic field and the RF pulse applied thereto;

acquiring MR signals from the part of the patient in a receive stage;

carrying out signal processing on the acquired signals by which an image is generated;

providing a plurality of surface electrodes attached to the skin of the patient at spaced positions on the skin for communicating electrical currents through the skin;

the surface electrodes each including a communication conductor for carrying the current;

wherein each of the surface electrodes comprises a layer having a bottom surface attached to the skin, the layer having a conductive location thereon connected to the communication conductor;

and reducing artifacts in the generated image by dividing the layer into separate side by side sections where the separation into the side by side sections is arranged to reduce eddy currents which are induced in the surface electrodes when they are exposed to variations in the magnetic field and to RF pulses;

the side by side sections being divided so that all are connected through the layer to the conductive location to allow the current to be connected to the communication conductor.

According to a second aspect of the invention there is provided a surface electrode to be attached to the skin of the patient for communicating current through the skin of the patient, the electrode being arranged to remain in place during an MR imaging method having a magnetic field, the electrode comprising:

a communication conductor for carrying current;

a layer having a bottom surface attached to the skin, the layer having a conductive location thereon connected to the communication conductor;

the layer being divided into separate side by side sections by slits in the layer arranged to reduce eddy currents which are induced in the surface electrodes when they are exposed to variations in the magnetic field;

the side by side sections being divided so that all are connected through the layer to the conductive location to allow the signal therefrom to be connected to the communication conductor.

The principles described in the application can be applied to any conductive surfaces used on the skin of the patient within a MRI scanner, for example, ECG electrodes, defibrillator pads. One particularly important function is that of catheter tracking to support electrophysiology where the combination of the electrophysiology with MRI provides particularly advantages for the patient.

Preferably in the above arrangements, the layer is formed of a non-ferromagnetic metal.

Preferably in the above arrangements, the layer is formed of silver-silver chloride.

Preferably in the above arrangements, the sections are formed in the layer by slits dividing each section from the next so that the eddy currents cannot bridge the slits.

In some cases in the above arrangements, the slits extend to the edge of the layer, however the slits may extend only partly along the layer from a position spaced from one edge of the layer a position spaced from the other edge, since the slits will act to reduce the eddy currents at their location while allowing eddy currents in parts which are not slit.

Preferably in one embodiment, the conductive location is arranged along one edge of the layer and the layer is divided into sections generally transverse to the edge.

Preferably in one embodiment, the conductive location is arranged in a central region of the layer and the layer is divided into sections extending generally outwardly from the central region.

Preferably in one embodiment, the sections extend generally radially from the central region.

Preferably in one embodiment, the sections include at least parts which extend generally angularly around the central region.

Preferably in the above arrangements, there is provided a quick connection coupler between the conductive location and the communication conductor so as to allow removal of the communication conductor during the MR imaging.

This invention address the two problematic aspects of introducing conventional surface electrodes into an interventional setting that uses MR at the end of the procedure.

Firstly eddy currents in the patch part of the electrode are reduced by a cut or slit design which decreases the surface area and constrains the geometry in which the eddy currents can circulate. These slotted cuts are a specific pattern which has been determined by simulation of a patch model and subsequent testing with the MR scanner for both effects of the B0 and B1 fields. These cuts are effective both for eddy currents produced by magnetic gradients and RF fields of an MR scanner. The slit is made so that it preferably removes a minimal amount of material from the layer while maintain the complex impedance (resistance and capacitance) required to interact with the communicating system. However the slits or slots may be wider with material removed to leave a space.

Secondly induced currents in the wires connecting the surface electrodes to the monitoring system are eliminated. This is accomplished by a design that uses a coaxial cable with a quick disconnect. This leaves a residual length of cable connected to the patch. This cable length can be specified to achieve the minimal risk for heating when used with imaging in different field strength MRI scanners.

With these improvements, imaging can be done safely at the end of the intervention by leaving the slotted electrodes in place and by simply disconnecting the coaxial cable from the quick disconnect.

This invention reduces eddy currents and their impact on image quality and addresses induced currents in the wire by the RF pulses by implementing a quick disconnect from the surface electrode to the cable.

With these above issues addressed, the invention enables the surface electrodes to remain in place on the patient during the post-procedure MR imaging session. Then, in the case that further treatment is required, the setup for treatment is greatly simplified. Patient treatment can begin quickly as indicated by the post-procedure scan.

This invention relates to the system disclosed in PCT Published Application 2009/0306494 of the present applicant published Dec. 10 2009, the disclosure of which is incorporated herein by reference. The arrangement disclosed herein enables the above system by improving the workflow between X-ray fluoro-guided catheter interventions and post-intervention MR imaging. The novelty exists in a cut pattern that reduces the eddy current's effect on image quality as well as the type of connector and cable such that the connection/disconnection can be made quickly; that the length of cable, if any, remaining attached to the electrodes does not pose a burn risk to the patient, and integrating these elements (connector/cuts) without degrading the information that the electrode is originally intended to provide.

Enabling post-procedure MR with these devices, or components of these devices in place, is also critical for MR-only cardiac interventions.

Electrodes will continue to be valuable to monitor patients and track devices as MR becomes more integrated in interventions. The actions mentioned here, cuts and disconnects, are fundamental to enabling electrodes in this space.

BRIEF DESCRIPTION OF THE DRAWINGS

One embodiment of the invention will now be described in conjunction with the accompanying drawings in which:

FIGS. 5 to 9 are plan views of alternative embodiments of the electrodes of FIG. 1.

In the drawings like characters of reference indicate corresponding parts in the different figures.

DETAILED DESCRIPTION

Figure 1:
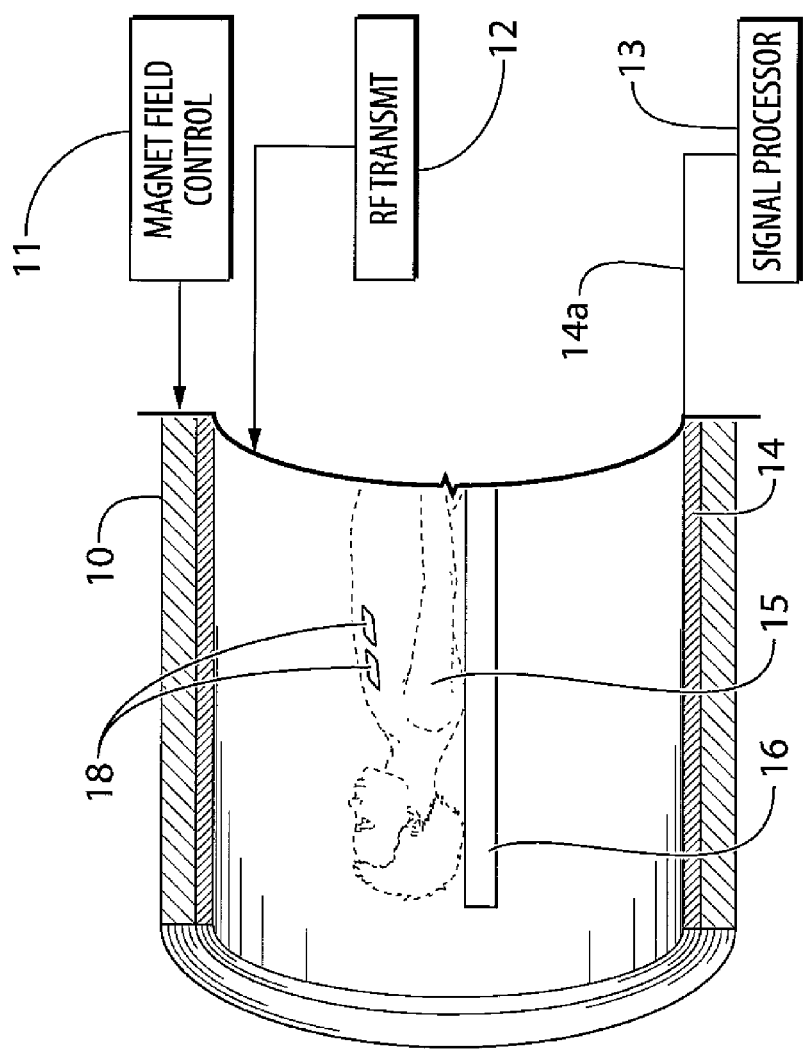
FIG. 1 is a schematic illustration of an MRI system including electrodes according to the present invention.

The apparatus for MR imaging of a subject includes a conventional cylindrical MR magnet 10 operable by a field control system to generate a variable magnetic field to be applied to the subject.

The MR system includes an RF transmit arrangement 12 for generating RF pulses in a transmit stage to be applied to the subject to be imaged and a receive arrangement for acquiring the MR signal in a receive stage with a signal processing system 13 for receiving the MR signal for carrying out signal processing by which an image is generated. A subject 15 is carried on a table 16 located within the imaging space of the magnet 10. As is well known, the subject generates an MR signal in response to the magnetic field and the RF signal applied which is detected and processed to generate an image. The arrangement is well known and a suitable system is available from Siemens.

Typically the magnet 10 carries an RF coil known as a body coil 14 which is mounted on the cylindrical magnet housing so as to surround the patient. This is usually used as the transmit coil. However separate transmit coils can be used. The body coil can also operate as the receive coil. However again separate receive coils can be used. The transmit and receive coils can be the same coils or can be provided by separate coils.

In the present arrangement, the subject has adhesive electrodes 18 applied to the surface of the skin which remain in place during the MR imaging Thus the plurality of surface electrodes 18 are attached to the skin of the patient at spaced positions on the skin for communicating electrical currents through the skin.

The surface electrodes 18 each include a layer 17 of a conductive material attached by a layer 19 of an adhesive material to the skin 25 of the patient. The adhesive and the layer 17 are formed of conventional materials suitable for EEG or defibrillator purposes which is typically a non-ferromagnetic metal and more typically silver-silver chloride. The layer includes a conductive location 20 thereon connected to a communication conductor 21 for carrying the current either to or from the layer depending upon the operation.

Artifacts in the generated image are reduced by dividing the layer 17 by slits 24 into separate side by side sections 17A, 17B, 17C and 17D where the separation into the side by side sections is arranged to reduce eddy currents which can be otherwise induced in the surface electrodes when they are exposed to variations in the magnetic field and to RF pulses.

The slits are arranged in the layer to remove only sufficient material to prevent direct communication of current across the slit from one section to the next. In this way any eddy currents forming in one section cannot bridge across from one section to the next and thus the eddy current being formed is suppressed by the reduction in the area in which it can form. A cutting technique for the slits can be used which removes only sufficient material to prevent direct contact side to side of the sections. Water jet cuffing is preferable over laser cutting which can burn portions of the material during processing. However other cutting or stamping techniques can be used. The slits in the layer are formed in a manner that the adhesive layer 19 remains intact through the whole of the underside of the layer 17. In this way the layer 19 retains the integrity of the electrode so that it can be applied to the skin of the patient.

The slits are narrow and remove little of the total area so as to avoid reducing the current transfer to the skin. Although an approximation, the resistance of a surface area of a conductive material is directly proportional to the surface area (A) of the material, to the resistivity ($\rho_s$) of the material and inversely proportional to the length of the sample (l). In addition from Faraday's law it can be easily shown that the induced voltage on a conductive surface area is directly proportional to the magnitude and frequency of the time dependent field as well as the surface area of the sample. Combining this with Ampere's law, the induced current to a give surface of a conductive material is directly proportional to the square of the surface of the material and inversely proportional to the material's resistivity and its effective length.

In order to reduce heating of the layer in the magnetic field the effective flowing current on the surface area of the electrode needs to be reduced. Since the frequency and magnitude of the magnetic field is given for a certain field strength, the only thing that it can adjusted is effective area of the electrode in which the current can be generated and the effective length. Thus by having narrow slits on the surface area of the electrode effectively reduces significantly the effective area that a current can flow from a time dependent magnetic field. Since heat is power and power is proportional to the square of the induced current and the electrode's resistance, reducing the effective area of the electrode where the induced current can flow acts to reduce the generated power to the fifth order. Thus the effective eddy current will be reduced proportionally to the square of the surface area of each surface portion defined between the slits. This reduction in the eddy currents avoids artifacts in the image so that no dark bands appear next to the electrodes, while the power is reduced to the fifth order of the area and the induced heat is significantly reduced.

The slots are preferably of a uniform width and are spaced uniformly across the patch as this simplifies the process of optimizing the design by simulation. The surface area of the patch is maximized by removing the minimum material in the slits to retain the electrical signal coupling between the patient's body and the patch. The slots preferably do not extend to the perimeter of the patch as doing so makes it more difficult to apply the patch to the patient's body. The slots avoid areas of the patch where the communicating wire is connected. Typically this communicating wire is splayed out in a small area of the patch on one side. The number of slots, the width of the slots and the spacing between slots can be varied but typical numbers are: 8-12 slots, 1-2 mm slot width, 10-15 mm spacing between slots.

The side by side sections are divided so that all are connected through the layer to the conductive location 20 where the wire 21 is connected and the individual wires 21C of the multi-strand wire 21 are located to allow the current to be connected to the wire 21. Thus each section has a direct conductive connection through the layer to the conductive location. In this way there is no interference with the communication of the current from each section to the conductive location 20. Thus the area of skin covered by the layer 17 remains fully in contact with the layer apart from the very narrow slits so that the communication from the conductive location to the area of skin remains unchanged by the presence of the slits.

Figure 2:
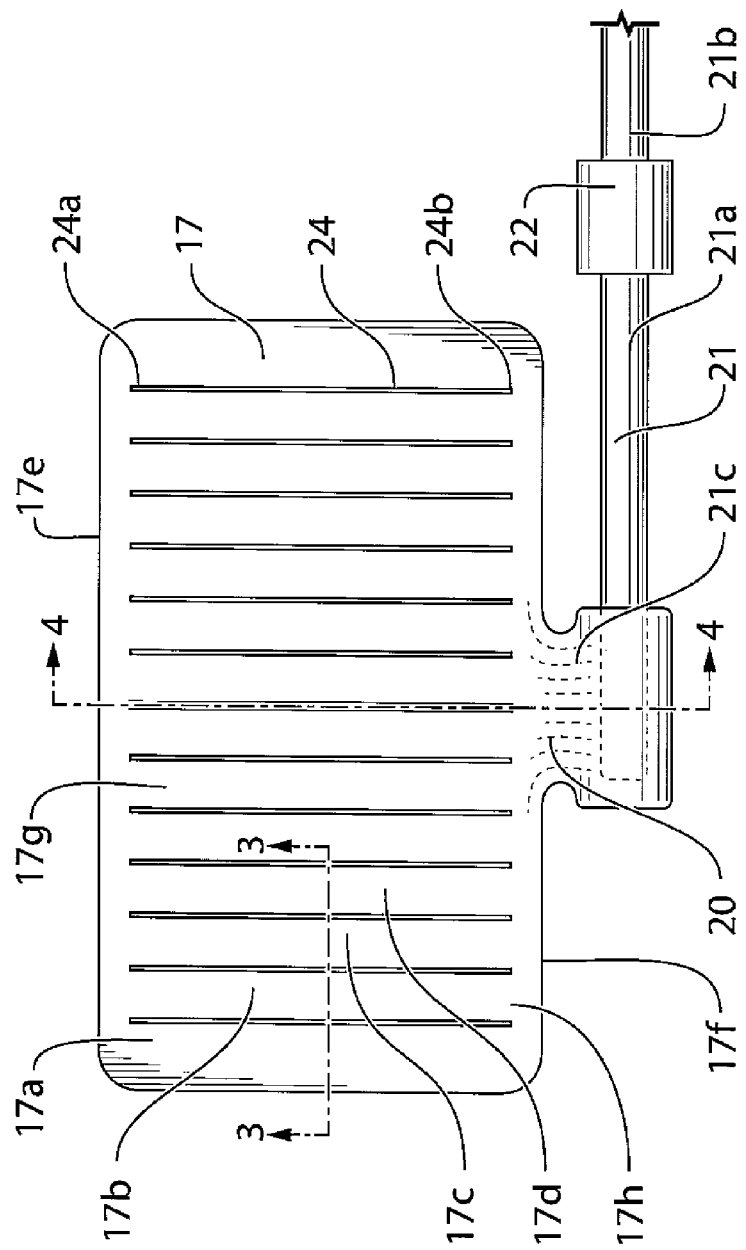
FIG. 2 is a plan view of one of the electrodes of FIG. 1.
Figure 3:
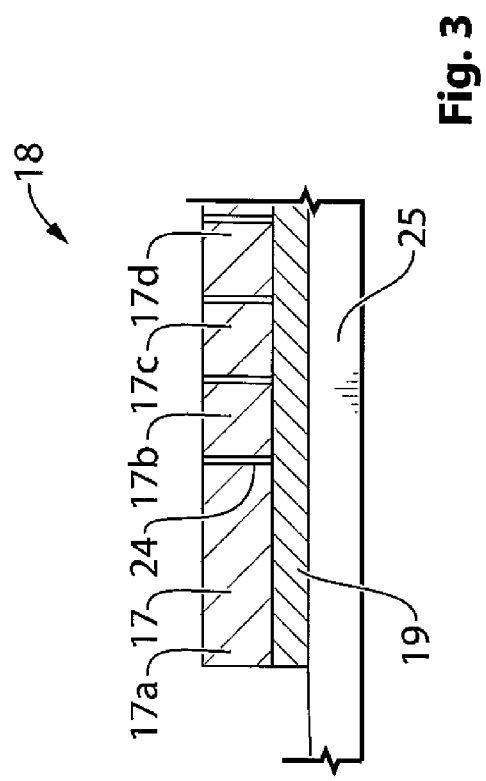
FIG. 3 is a cross-sectional view along the lines 3-3 of FIG. 2.
Figure 4:
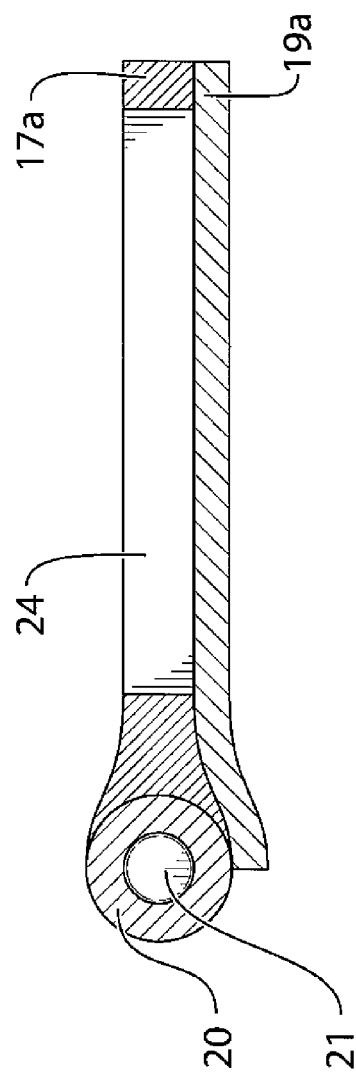
FIG. 4 is a cross-sectional view along the lines 4-4 of FIG. 2.
Figure 7:
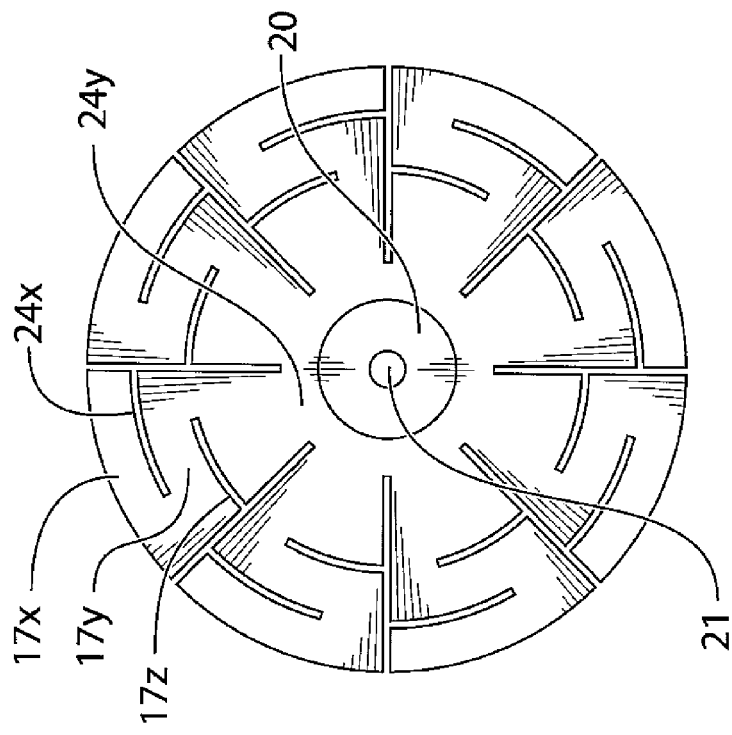
Figure 8:
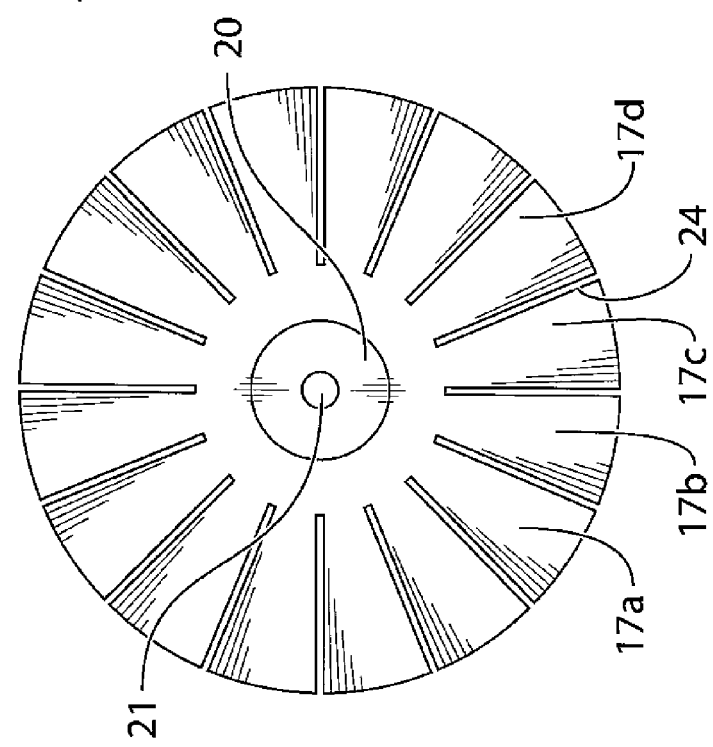

In FIG. 2 the slits extend to ends 24A, 24B located at a position spaced from the edge 17E, 17F of the layer. This in effect forms another section 17G along the edge 17E and a section 17H along the edge 17F. Thus each section 17A, 17B, 17C, 17D, 17G, 17H is relatively narrow and long to reduce eddy current formation but each section can communicate directly to the conductive location 20 without any significant increase in resistance. The sections are approximately of the same width.

The impedance (resistance and capacitance) of the modified patches are designed to match the original unmodified patch impedance expected by the system within reasonable tolerances.

Figure 9:
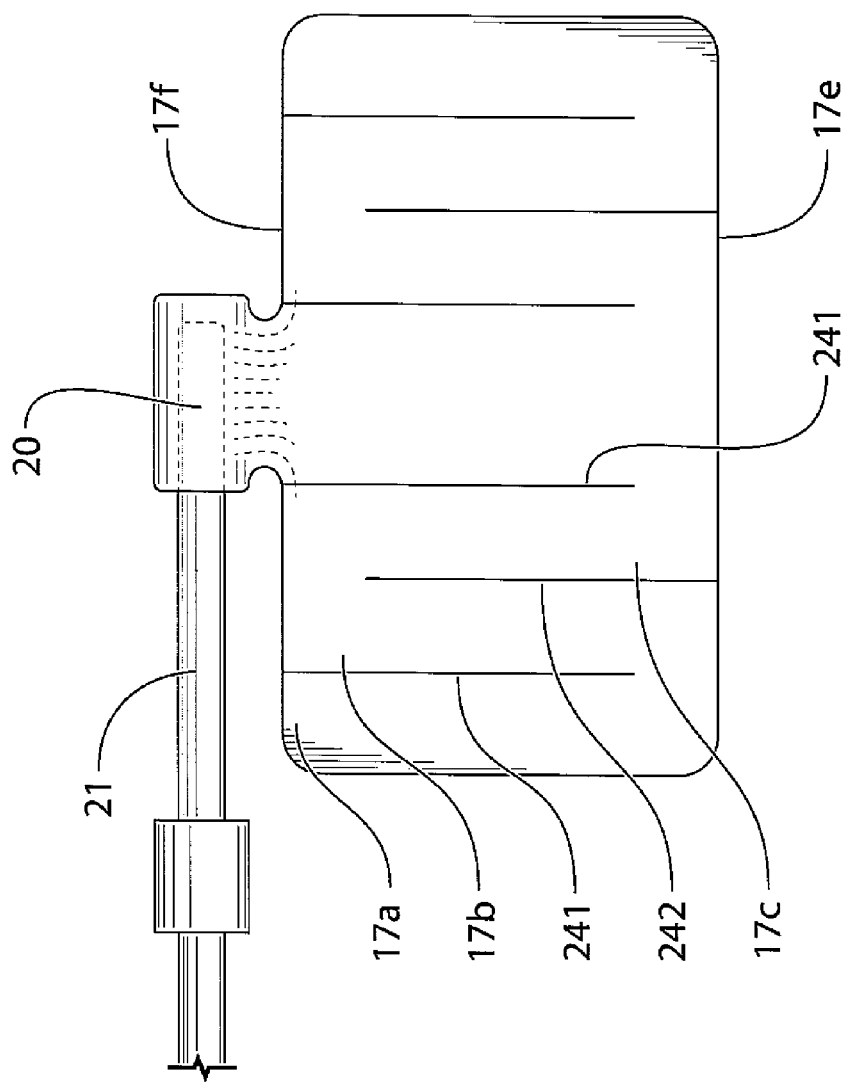

In FIG. 9 the slits 241, 242 extend to the edges 17F and 17G respectively of the layer 17 but again there is direct connection to the conductive location 20 from the outermost section 17A through the sections 17B and 17C to the central strip 17D connected to the conductive location 20.

As shown in FIGS. 2 and 9, the layer is generally rectangular with the conductive location 20 arranged along one edge of the layer and the layer is divided into the sections 17A to 17D generally transverse to the edge 17E. The conductor 21 lies along the edge 17E in a common plane therewith.

The conductor 21 is a conventional coaxial cable with a central conductor carrying the signal surrounded by a layer of an insulation material, a braided shielding and a jacket. The conductor 21 includes a quick release connector 22. This is of a conventional arrangement such as a Rosenberger 19K102-101L5-NM SMP straight jack which connects to a connector RG-178 on the crimping end and SMP right angle connector on the other end.

In an alternative arrangement shown in FIGS. 5 to 8, the conductive location 20 is arranged in a central region of the a circular layer with the conductor and the layer is divided into sections extending generally outwardly from the central region. Thus in FIGS. 6 to 8, the sections and the slits therebetween extend generally radially from the central region. The conductor 21 extends at right angles to the layer that is away from the body of the patient and includes a connector 22 (not shown).

In FIG. 9, the sections and slits therebetween include at least parts 17X, 17Y and 17Z are separated by slit lines 24X and 24Y which extend generally angularly around the central region.

The quick connection coupler 22 is arranged in the communication conductor 21 between portions 21A and 21B at a position adjacent to the conductive location 20 but spaced outwardly therefrom to define a portion 21A of the communication conductor between the conductive location 20 and the quick connection coupler 22 which has a length arranged to minimize heating of the portion.

A variety of sizes and shapes of surface electrodes can be used. The slots are designed not to interfere with the splayed out braided wire of the conductor 21 which provides the electrical interface between the communicating cable and the conductive surface. Some designs are irregular due to their anatomical placement and the importance of providing access for ECG electrodes adjacent to the surface electrode. Sizes vary between adult and pediatric patches and for patches used in various locations.

The quick disconnect coupling 22 is formed by cutting the cable connecting to the electrode 5 cm from the electrode. A determination is made of the cable length required and the cable is cut it from the coaxial cable such as cable type RG-178 which is a coaxial cable commonly used for high frequency signal transmission.

An SMP connector is attached to the RG-178 cable. The connection is wrapped by heat shrink material or tape to provide the connection with the required stability. The wire end which hangs over the PCB is wrapped in electrical tape, using adhesive to secure the wire to the PCB, and the entire assembly is wrapped with the heat shrink material.

The loose end of the RG-178 cable may require a special end to be connected to ensure that the center pin of the cable is used as the active connection.

In the arrangement of FIG. 2, the electrode 1.5 mm cuts every 2 cm which extend 1.3 cm from a position adjacent the lead edge 17F to a position adjacent the edge 17E.

In the arrangement of FIG. 9, the electrode has 1.5 mm cuts every 2 cm which extend 1.3 cm from alternating edges.

The invention claimed is:

1. A method of magnetic resonance (MR) imaging of a patient comprising;
    providing an MR magnet in order to generate a magnetic field that is applied to the patient;
    providing a plurality of surface electrodes which are then attached to the skin of the patient, at spaced positions on the skin, with the plurality of surface electrodes being configured for communicating electrical currents through the skin;
    utilizing the plurality of surface electrodes, with each one of the plurality of surface electrodes including:
        a communication conductor that is configured for carrying the current;
        wherein each of the plurality of surface electrodes also comprises an electrically conductive layer having a bottom surface that is also attached to the skin of the patient; and
        wherein the conductive layer, of each of the plurality of surface electrodes has a conductive location portion of the electrically conductive layer that is connected to the communication conductor of each respective electrode within the plurality of surface electrodes;
        dividing and separating the electrically conductive layer which is part of each individual surface electrode into separate side by side sections;
        communicating the electrical currents between the skin of the patient and the communication conductor through the separate side by side sections, by dividing and separating the side by side sections so that all the side by side sections within the plurality of surface electrodes are connected through the electrically conductive layer in order to connect to the conductive location portion of the electrically conductive layer, of each respective surface electrode, within the plurality of surface electrodes;
    generating an RF pulse in the magnetic field that is applied to the patient such that the imaged part of the patient generates an MR signal in response to the provided magnetic field and the generated RF pulse applied thereto;
    acquiring MR signals from the imaged part of the patient in a receive stage of the magnetic resonance imaging method;
    carrying out signal processing on the MR acquired signals by which a magnetic resonance image is generated; and
    reducing artifacts produced by each individual surface electrode in the generated magnetic resonance image by dividing and separating the electrically conductive layer which is part of each individual surface electrode into said separate side by side sections, where the division and separation of each electrically conductive layer into the side by side sections is arranged in order to reduce eddy currents which are induced in a respective electrically conductive layer when that respective electrically conductive layer is exposed to variations in the magnetic field and to variations in the RF pulses.

2. The method according to claim 1 wherein the electrically conductive layer within the plurality of surface electrodes is formed of a non-ferromagnetic conductive metal.

3. The method according to claim 1 wherein the electrically conductive layer within the plurality of surface electrodes is formed of silver-silver chloride.

4. The method according to claim 1 wherein the side by side sections are formed in the electrically conductive layer, of each of the plurality of surface electrodes, by slits dividing each side by side section from the next, whereby the eddy currents cannot bridge the slits.

5. The method according to claim 1 wherein the slits extend to an edge of each respective electrically conductive layer within the plurality of surface electrodes.

6. The method according to claim 1 wherein the slits extend to a position spaced from an edge of each respective electrically conductive layer within the plurality of surface electrodes.

7. The method according to claim 6 wherein the conductive location portion of each respective electrode within the plurality of surface electrodes, is arranged along said edge of the electrically conductive layer, of each of the plurality of surface electrodes, and the electrically conductive layer of each of the plurality of surface electrodes, is divided into sections generally transverse to the edge.

8. The method according to claim 1 wherein the electrically conductive layer of each of the plurality of surface electrodes, includes an adhesive layer on the bottom surface configured for adhesive attachment of the electrically conductive layer to the skin of the patient.

9. The method according to claim 8 wherein the side by side sections are formed in the electrically conductive layer, of each of the plurality of surface electrodes, by slits dividing each side by side section from the next;
    whereby the eddy currents cannot bridge the slits; and
    wherein the adhesive layer forms an integral layer bridging the slits.

10. The method according to claim 1 wherein the conductive location portion of each respective electrode within the plurality of surface electrodes, is arranged in a central region of the electrically conductive layer; and
    the electrically conductive layer of each of the plurality of surface electrodes, is divided into said side by side sections extending generally outwardly from the central region.

11. The method according to claim 10 wherein the side by side sections of each electrically conductive layer extend generally radially from the central region.

12. The method according to claim 10 wherein the side by side sections of each electrically conductive layer include at least parts which extend generally angularly around the central region.

13. The method according to claim 1 wherein within each of the plurality of surface electrodes there is provided a quick connection coupler in order to allow removal of the communication conductor from the conductive location portion during the performance of the MR imaging method.

14. The method according to claim 13 wherein within each of the plurality of surface electrodes, the quick connection coupler is arranged in the communication conductor at a position that is closely adjacent to the conductive location portion.

15. The method according to claim 1 wherein each of the surface electrodes is a sensing electrode configured for use in sensing electrical signals within the body of the patient.

16. The method according to claim 1 wherein each of the surface electrodes is arranged and configured for use in applying electrical currents to the body of the patient.

17. A surface electrode configured to be attached to the skin of the patient and configured for communicating electrical currents through the skin of the patient, the surface electrode being arranged in order to remain in place during a magnetic resonance (MR) imaging method having a magnetic field, the surface electrode comprising:
a communication conductor configured for carrying the electrical currents;
an electrically conductive layer having a bottom surface arranged to be attached to the skin of the patient;
wherein the electrically conductive layer of the surface electrode has a conductive location portion of the electrically conductive layer connected to the communication conductor;
the electrically conductive layer being divided into separate side by side sections, of the electrically conductive layer, by slits in the electrically conductive layer arranged in order to reduce eddy currents, which are induced in the electrically conductive layer, when the electrically conductive layer is exposed to variations in the magnetic field;
the side by side sections of the surface electrode being divided whereby all the side by side connections of the surface electrode are connected through the electrically conductive layer in order to connect to the conductive location portion of the electrically conductive layer and allow the current to be connected between the skin of the patient and the communication conductor.

18. The surface electrode according to claim 17 wherein the electrically conductive layer includes an adhesive layer on the bottom surface configured for adhesive attachment of the electrically conductive layer to the skin of the patient.

19. The surface electrode according to claim 18 wherein the adhesive layer forms an integral layer bridging the slits in the electrically conductive layer.

20. The surface electrode according to claim 18 wherein the surface electrode is a sensing electrode configured for use in sensing electrical signals within the body of the patient.

\* \* \* \* \*